US008562747B2

(12) United States Patent  (10) Patent No.: US 8,562,747 B2
Nagahama et al.  (45) Date of Patent: Oct. 22, 2013

(54) METHOD AND SYSTEM FOR HYDROLYTIC SACCHARIFICATION OF A CELLULOSIC BIOMASS

(75) Inventors: Takeshi Nagahama, Kobe (JP); Noriaki Izumi, Kobe (JP)

(73) Assignee: Kawasaki Plant Systems Kabushiki Kaisha, Kobe-shi (JP)

(*) Notice: Subject to any disclaimer, the term of this patent is extended or adjusted under 35 U.S.C. 154(b) by 54 days.

(21) Appl. No.: 13/451,858

(22) Filed: Apr. 20, 2012

(65) Prior Publication Data

US 2012/0255543 A1  Oct. 11, 2012

Related U.S. Application Data

(62) Division of application No. 12/063,757, filed as application No. PCT/JP2007/070600 on Oct. 23, 2007, now abandoned.

(30) Foreign Application Priority Data

Oct. 26, 2006 (JP) .................................. 2006-291194

(51) Int. Cl.
  *C13K 1/02* (2006.01)
(52) U.S. Cl.
  USPC .......................................................... 127/37
(58) Field of Classification Search
  None
  See application file for complete search history.

(56) References Cited

U.S. PATENT DOCUMENTS

| | | | |
|---|---|---|---|
| 4,470,851 | A | 9/1984 | Paszner et al. |
| 4,520,105 | A | 5/1985 | Sinner et al. |
| 4,742,814 | A | 5/1988 | Sinner et al. |
| 4,941,944 | A | 7/1990 | Chang |
| 4,992,105 | A | 2/1991 | Werner et al. |
| 5,888,307 | A | 3/1999 | Solheim |
| 2003/0234212 | A1 | 12/2003 | Ito et al. |

FOREIGN PATENT DOCUMENTS

| | | |
|---|---|---|
| JP | 54-070444 | 6/1979 |
| JP | 58-500431 | 3/1983 |
| JP | 61-010009 | 1/1986 |
| JP | 62-011501 | 1/1987 |
| JP | 2000-186102 | 7/2000 |
| JP | 2002-059118 | 2/2002 |
| JP | 2002-233400 | 8/2002 |
| JP | 2003-212888 | 7/2003 |
| JP | 2006-223152 | 8/2006 |
| WO | WO-82/03409 | 10/1982 |
| WO | WO-96/09882 A1 | 4/1996 |
| WO | WO-96/25553 A1 | 8/1996 |

*Primary Examiner* — Curtis Mayes
*Assistant Examiner* — Bijay Saha
(74) *Attorney, Agent, or Firm* — Marshall, Gerstein & Borun LLP

(57) ABSTRACT

A method and system for hydrolyzing cellulose and/or hemicellulose contained in a biomass into monosaccharides and oligosaccharides by using high-temperature and high-pressure water in a subcritical condition is provided. In hydrolyzing cellulose or hemicellulose into saccharides by using high-temperature and high-pressure water in a subcritical condition, a large amount of slurry is cooled into a condition below the subcritical condition by subjecting the slurry contained in a pressure vessel under a high-temperature and high-pressure condition to flash evaporation in a pressure vessel charged with a slurry of a cellulosic biomass and heated halfway. It is possible to prevent saccharides from degrading into organic acids and to save energy by recovery of thermal energy. The cellulosic biomass is charged into a water-permeable vessel and then the water-permeable vessel is encapsulated into the pressure vessel together with water.

5 Claims, 6 Drawing Sheets

METHOD AND SYSTEM FOR HYDROLYTIC SACCHARIFICATION OF A CELLULOSIC BIOMASS

CROSS REFERENCE TO RELATED APPLICATIONS

This application is a divisional of U.S. patent application Ser. No. 12/063,757, filed Feb. 1, 2010, now abandoned, which in turn is a U.S. National Phase of PCT/JP2007/070600, filed Oct. 23, 2007, which in turn claims foreign priority of Japanese Application No. 2006291194, filed Oct. 26, 2006, the disclosures of which are incorporated herein by reference in their entirety.

BACKGROUND OF THE INVENTION

1. Field of the Invention

The present invention relates to a hydrolyzing method and system for efficiently producing saccharides from biomasses, particularly cellulosic biomasses, used as raw materials.

2. Description of the Related Art

As part of biomass energy utilization, attempts have been made to obtain ethanol (bioethanol) by hydrolyzing cellulose or hemicellulose, which are major constituents of plants. Ethanol thus obtained is planned to be utilized as a fuel to be mixed into an automotive fuel or as an alternative fuel for gasoline.

Major constituents of plants include cellulose (a polymer of glucose, which is a C6 saccharide comprising six carbon atoms), hemicellulose (a polymer of a C5 saccharide comprising five carbon atoms and a C6 saccharide), lignin, starch, and the like. Ethanol is produced from saccharides, such as a C5 saccharide, C6 saccharide, and oligosaccharide which is a complex of these saccharides, used as raw materials, by the fermentation action of yeast fungi or the like.

Three methods of hydrolyzing a cellulosic biomass comprising cellulose, hemicellulose or the like into saccharides are about to be utilized industrially, which include: 1) a method of hydrolyzing such a biomass by the oxidative power of a strong acid, such as sulfuric acid; 2) a method of hydrolyzing such a biomass by yeast; and 3) a method utilizing the oxidative power of supercritical water, subcritical water or the like. However, the hydrolytic method 1) using the acid indispensably requires a treatment for neutralizing the added acid after hydrolysis of cellulose or hemicellulose into saccharides and before fermentation of the saccharides into ethanol because the added acid acts as an inhibitor against the fermentation by yeast or the like. The cost of such a treatment makes it difficult to put this method into practice in view of the economical aspect.

The outlook for industrial-scale realization of the hydrolyzing method 2) using yeast is still vague in view of the cost efficiency because an effective yeast for the method 2) has not been found yet and, if found, such a yeast is expected to incur a high production cost thereof, though the method 2) can be realized by a normal-temperature and normal-pressure process.

As the method 3) of hydrolyzing cellulose or the like into saccharides by using supercritical or subcritical water, patent document 1 has disclosed a method of producing water-insoluble polysaccharides, which is characterized by hydrolysis of cellulosic powder by bringing the powder into contact with pressurized hot water at 240 to 340° C. Patent document 2 has disclosed a method including: hydrolyzing biomass chips with hot water pressurized to a saturated vapor pressure or more at 140 to 230° C. for a predetermined time period to extract hemicellulose; and then conducting hydrolysis using pressurized hot water heated to a temperature not less than the cellulose hydrolyzig temperature to extract cellulose. Patent document 3 has disclosed a method of producing glucose and/or water-soluble cello-oligosaccharide, which is characterized in that cellulose having a mean polymerization degree of not less than 100 is hydrolyzed by the steps of: bringing the cellulose into contact with supercritical or subcritical water at a temperature of not lower than 250° C. and not higher than 450° C. and a pressure of not less than 15 Mpa and not more than 450 MPa for a time period of not less than 0.01 seconds and not more than 5 seconds; cooling the cellulose; and then bringing the cellulose into contact with subcritical water at a temperature of not lower than 250° C. and not higher than 350° C. and a pressure of not less than 15 Mpa and not more than 450 MPa for a time period of not less than 1 seconds and not more than 10 minutes.

On the other hand, patent document 4 has disclosed a method of treating a biomass-type waste, which includes: placing a subject for treatment containing a solvent comprising low-molecular-weight alcohol as a major component and the biomass-type waste into a closed vessel; and treating the subject by pressurizing and heating the interior of the closed vessel so that the low-molecular-weight alcohol reaches its supercritical condition. Also, patent document 5 has disclosed a method of hydrolyzing and liquefying a biomass, which includes treating a cellulosic biomass by using a mixed solvent prepared by adding 5-20% by volume of water to a C1 to C8 aliphatic alcohol under the supercritical or subcritical condition of the alcohol.

Patent document 1: Japanese Patent Provisional Publication No. 2000-186102
Patent document 2: Japanese Patent Provisional Publication No. 2002-59118
Patent document 3: Japanese Patent Provisional Publication No. 2003-212888
Patent document 4: Japanese Patent Provisional Publication No. 2001-170601
Patent document 5: Japanese Patent Provisional Publication No. 2005-296906

As compared with the hydrolytic method using a strong acid, the method of hydrolytic saccharification of cellulose and hemicellulose as major constituents of a biomass by using high-temperature and high-pressure supercritical or subcritical water requires a lower processing cost and is a more environment friendly because this method does not require any acid neutralizing treatment. However, this method has a drawback that without cooling immediately after the completion of hydrolysis, saccharides produced thus far would degrade into organic acids or the like because the use of supercritical or subcritical water causes cellulose and hemicellulose to hydrolyze into saccharides completely in several seconds to several minutes by its strong oxidative power.

With a laboratory-scale small system for hydrolysis, it seems that such degradation can be prevented by rapidly cooling supercritical or subcritical water in the heating vessel. With an industrial-scale hydrolysis system, however, it is very difficult to cool a large amount of supercritical or subcritical water in a short time. For this reason, the cellulosic biomass hydrolysing method using high-temperature and high-pressure supercritical or subcritical water, when applied to a plant-scale system, will give a low yield of saccharides, which forms one of the factors that prevent this method from being put to practice.

In using a large amount of supercritical or subcritical water, the slurry has to be heated with a large amount of energy, which forms a factor raising the processing cost. The cellulosic biomass hydrolyzing method, which subjects a slurry containing alcohol or the like as a solvent to hydrolysis under a supercritical or subcritical condition, requires a very high vapor pressure, hence, requires a larger amount of energy and has to use a system having a high pressure resistance.

It is an object of the present invention to provide a method and system for hydrolyzing cellulose and/or hemicellulose contained in a biomass into monosaccharides and oligosaccharides (hereinafter will be referred to as "saccharides") by using high-temperature and high-pressure water in a subcritical condition, which method and system is excellent in thermal efficiency and yields of saccharides.

SUMMARY OF THE INVENTION

The inventor of the present invention has found out that in hydrolyzing cellulose or hemicellulose into saccharides by using high-temperature and high-pressure water in a subcritical condition it is possible to cool a large amount of slurry to a temperature not higher than the cellulose hydrolyzing temperature thereby preventing saccharides from degrading into organic acids or the like as well as to save energy by recovery of thermal energy, by subjecting the slurry contained in a pressure vessel under a high-temperature and high-pressure condition to flash evaporation in a pressure vessel that is charged with a slurry of a cellulosic biomass and heated halfway. Thus, the present invention has been accomplished.

Specifically, the present invention is directed to a method of hydrolytic saccharification of a cellulosic biomass with use of plural pressure vessels, the method comprising a charging step, a heating-up step, a hydrolyzing step, a temperature lowering step, and a discharging step, which are performed sequentially by each of the pressure vessels, wherein:

the charging step is a step of charging a slurry prepared by grinding the cellulosic biomass and then mixing the cellulosic biomass thus ground with water (hereinafter will be referred to as "slurry") into each of the pressure vessels;

the heating-up step is a step of hermetically closing the pressure vessel and heating up the slurry;

the hydrolyzing step is a step of hydrolyzing cellulose and/or hemicellulose contained in the cellulosic biomass into saccharides by an oxidative power of high-temperature and high-pressure water;

the temperature lowering step is a step of flash-evaporating the high-temperature and high-pressure slurry contained in the pressure vessel to flash evaporation to lower the temperature thereof;

the discharging step is a step of removing the slurry out of the pressure vessel;

while any one of the plural pressure vessels performs the charging step, any one of the other pressure vessels performs the discharging step so as to allow heat exchange to occur between the slurry to be charged into the pressure vessel performing the charging step and the slurry to be discharged from the pressure vessel performing the discharging step; and while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

The present invention is also directed to a system for hydrolytic saccharification of a cellulosic biomass, comprising plural pressure vessels each configured to perform sequential steps including:

a charging step of charging a slurry prepared by grinding the cellulosic biomass and then mixing the cellulosic biomass thus ground with water into the pressure vessel;

a heating-up step of hermetically closing the pressure vessel and heating up the pressure vessel;

a hydrolyzing step of hydrolyzing cellulose and/or hemicellulose contained in the cellulosic biomass into saccharides by an oxidative power of high-temperature and high-pressure water;

a temperature lowering step of flash-evaporating the high-temperature and high-pressure slurry contained in the pressure vessel to lower the temperature thereof; and a discharging step of removing the slurry out of the pressure vessel, wherein:

while any one of the plural pressure vessels performs the charging step, any one of the other pressure vessels performs the discharging step so as to allow heat exchange to occur between the slurry to be charged into the pressure vessel performing the charging step and the slurry to be discharged from the pressure vessel performing the discharging step; and while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

In the method and system for hydrolytic saccharification of a cellulosic biomass according to the present invention, five process steps are performed in each of the plural pressure vessels. By connecting the pressure vessel at the temperature lowering step to another pressure vessel at the heating-up step, the slurry in the pressure vessel at the temperature lowering step can be rapidly cooled by flash evaporation. At the same time, the slurry in the pressure vessel performing the heating-up step can be heated by high-temperature flash vapor, whereby the energy required to heat the slurry can be saved.

By reducing the internal pressure of the pressure vessel from the gas phase portion, there is no danger that the dissolved components and solid contents of the slurry move to clog the nozzle and piping for passage of flash vapor. Further, there is no need to provide a special temperature controller or the like. In supplying the preheated side (i.e., the pressure vessel at the heating-up step) with flash vapor, the preheating of the slurry becomes more effective by supplying flash vapor into the slurry.

The method and system for hydrolytic saccharification of a cellulosic biomass according to the present invention allows heat exchange to occur between the slurry to be discharged (drained) from the pressure vessel at the discharging step and the slurry to be charged into another pressure vessel at the charging step, thereby making it possible to further save the energy required to heat the slurry.

The present invention is also directed to a method of hydrolytic saccharification of a cellulosic biomass with use of plural pressure vessels, the method comprising a charging step, a heating-up step, a hydrolyzing step, a temperature lowering step, and a discharging step, which are performed sequentially by each of the pressure vessels, wherein:

the charging step is a step of charging the cellulosic biomass into a water-permeable vessel and then encapsulating the water-permeable vessel and water into each of the pressure vessels;

the heating-up step is a step of hermetically closing the pressure vessel and heating up the cellulosic biomass and water;

the hydrolyzing step is a step of hydrolyzing cellulose and/or hemicellulose contained in the cellulosic biomass into saccharides by an oxidative power of high-temperature and high-pressure water;

the temperature lowering step is a step of flash-evaporating high-temperature and high-pressure water contained in the pressure vessel to lower the temperature thereof;

the discharging step is a step of removing the water and the water-permeable vessel out of the pressure vessel;

while any one of the plural pressure vessels performs the charging step, any one of the other pressure vessels performs the discharging step so as to allow heat exchange to occur between water to be charged into the pressure vessel performing the charging step and high-temperature water to be discharged from the pressure vessel performing the discharging step; and while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

The present invention is also directed to a system for hydrolytic saccarification of a cellulosic biomass, comprising plural pressure vessels each configured to perform sequential steps including:

a charging step of encapsulating water and a water-permeable vessel charged with the cellulosic biomass into the pressure vessel;

a heating-up step of hermetically closing the pressure vessel and heating up the pressure vessel;

a hydrolyzing step of hydrolyzing cellulose and/or hemicellulose contained in the cellulosic biomass into saccharides by an oxidative power of high-temperature and high-pressure water;

a temperature lowering step of flash-evaporating high-temperature and high-pressure water contained in the pressure vessel to lower the temperature thereof; and a discharging step of removing a residue of the cellulosic biomass out of the pressure vessel, wherein:

while any one of the plural pressure vessels performs the charging step, any one of the other pressure vessels performs the discharging step so as to allow heat exchange to occur between water to be charged into the pressure vessel performing the charging step and high-temperature water to be discharged from the pressure vessel performing the discharging step; and while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

In hydrolyzing cellulose or hemicellulose into saccharides by using high-temperature and high-pressure water in a subcritical condition, the cellulosic biomass is charged into the water-permeable vessel having perforations, apertures or the like for allowing water to move from the exterior to the interior of the water-permeable vessel and vice versa and then the water-permeable vessel and water are encapsulated into each pressure vessel (compressive and dense encapsulation). By so doing, the vessels and associated piping can be prevented from being contaminated with fine residue of slurry.

In cases where equal time is required to complete respective of all the aforementioned five steps, the number of the pressure vessels used is preferably a multiple of five. With this feature, the sequential steps can be performed smoothly while performing heat recovery twice.

In cases where equal time is required to complete respective of all the four steps other than the hydrolyzing step and the time required to complete the hydrolyzing step is n times (where n is a natural number) as long as the time required to complete respective of all the other four steps, the number of the pressure vessels used is preferably a multiple of (4+n). Where the time required to complete the hydrolyzing step is n times as long as that required to complete any other step, the number of pressure vessels to perform the hydrolyzing step is preferably n times as large as the number of pressure vessels to perform the other steps. With this feature, the sequential steps can be performed smoothly while performing heat recovery twice.

When the hydrolyzing step is performed at a temperature of not lower than 140° C. and not higher than 180° C., hemicellulose can be hydrolyzed into saccharides (mainly including C5 monosaccharides). A biomass containing a large amount of hemicellulose is preferably processed under relatively moderate conditions because high-temperature processing causes C5 monosaccharides and the like to degrade into organic acids and the like.

Thereafter, the slurry resulting from the discharging step is subjected to solid-liquid separation; a solid content produced after elution of hydrolyzed hemicellulose to the solvent side is separated out for use as a fresh raw slurry; the raw slurry is subjected to the charging step again; and the hydrolyzing step is performed at a temperature of not lower than 240° C. and not higher than 280° C. By so doing, cellulose can be hydrolyzed into saccharides (mainly including C6 monosaccharides).

Alternatively, by subjecting the water-permeable vessel having been subjected to the discharge step to the charging step again and performing the hydrolyzing step at a temperature of not lower than 240° C. and not higher than 280° C., it is possible to hydrolyze cellulose into saccharides.

Hemicellulose contained in the biomass is first hydrolyzed into saccharides at a temperature of not lower than 140° C. and not higher than 180° C. and then the biomass is subjected to solid-liquid separation. By so doing, cellulose can be separated out as a solid. A slurry comprising the cellulose thus obtained is subjected to the charging step and then to the hydrolyzing step at a temperature of not lower than 240° C. and not higher than 280° C. By so doing, the cellulose can be hydrolyzed into saccharides. This process is effective for a biomass containing cellulose and hemicellulose in substantially equal amounts.

When the hydrolyzing step is performed at a temperature of not lower than 240° C. and not higher than 280° C., cellulose can be hydrolyzed into saccharides (mainly including C6 monosaccharides). In the case of a biomass having a high cellulose content, a process for hydrolyzing only cellulose into saccharides at a relatively high temperature is more effective because the necessity to take degradation of hemicellulose into consideration is low.

Preferably, the charging step includes addition of ethanol in an amount of not less than 2 mol % and not more than 10 mol % to the raw slurry or to water to be encapsulated in the pressure vessel step. The addition of a small amount of ethanol to the raw slurry causes the reaction rate of hydrolysis of cellulose and/or hemicellulose into saccharides by subcritical water to be lowered. Thus, the cellulose and/or hemicellulose hydrolysis time in the hydrolyzing step can be adjusted so as to facilitate inhibition of degradation into organic acids and the like, thereby raising the yield.

The present invention is also directed to a method of hydrolytic saccharification of a cellulosic biomass with use of plural pressure vessels, the method comprising a discharging and charging step, a heating-up step, a hydrolyzing step, and a temperature lowering step, which are performed sequentially by each of the pressure vessels, wherein:

the discharging and charging step is a step of removing a slurry out of each of the pressure vessel after the temperature lowering step and charging a slurry prepared by grinding the cellulosic biomass and mixing the cellulosic biomass thus ground with water into the same pressure vessel;

the heating-up step is a step of hermetically closing the pressure vessel and heating up the pressure vessel;

the hydrolyzing step is a step of hydrolyzing cellulose and/or hemicellulose contained in the cellulosic biomass into saccharides by an oxidative power of high-temperature and high-pressure water;

the temperature lowering step is a step of flash-evaporating the high-temperature and high-pressure slurry contained in the pressure vessel to lower the temperature thereof; and while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

The present invention is also directed to a system for hydrolytic saccharification of a cellulosic biomass, comprising plural pressure vessels each configured to perform sequential steps including:

a discharging and charging step of removing a high-temperature slurry out of the pressure vessel after a temperature lowering step and charging a slurry prepared by grinding the cellulosic biomass and then mixing the cellulosic biomass thus ground with water into the same pressure vessel;

a heating-up step of hermetically closing the pressure vessel and heating up the pressure vessel;

a hydrolyzing step of hydrolyzing cellulose and/or hemicellulose contained in the cellulosic biomass into saccharides by an oxidative power of high-temperature and high-pressure water; and the temperature lowering step of flash-evaporating the high-temperature and high-pressure slurry contained in the pressure vessel to lower the temperature thereof, wherein while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

The present invention is also directed to a method of hydrolytic saccharification of a cellulosic biomass with use of plural pressure vessels, the method comprising a discharging and charging step, a heating-up step, a hydrolyzing step, and a temperature lowering step, which are performed sequentially by each of the pressure vessels, wherein:

the discharging and charging step is a step of removing a cellulosic biomass residue out of each of the pressure vessels after the temperature lowering step and encapsulating water and a water-permeable vessel charged with the cellulosic biomass into the same pressure vessel;

the heating-up step is a step of hermetically closing the pressure vessel and heating up the pressure vessel;

the hydrolyzing step is a step of hydrolyzing cellulose and/or hemicellulose contained in the biomass into saccharides by an oxidative power of high-temperature and high-pressure water;

the temperature lowering step is a step of flash-evaporating high-temperature and high-pressure water contained in the pressure vessel to lower the temperature thereof; and while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

The present invention is also directed to a system for hydrolytic saccharification of a cellulosic biomass, comprising plural pressure vessels each configured to perform sequential steps including:

a discharging and charging step of removing a cellulosic biomass residue out of the pressure vessel after a temperature lowering step and encapsulating water and a water-permeable vessel charged with the cellulosic biomass into the pressure vessel;

a heating-up step of hermetically closing the pressure vessel and heating up the pressure vessel;

a hydrolyzing step of hydrolyzing cellulose and/or hemicellulose contained in the cellulosic biomass into saccharides by an oxidative power of high-temperature and high-pressure water; and the temperature lowering step of flash-evaporating high-temperature and high-pressure water contained in the pressure vessel to lower the temperature thereof, wherein while any one of the plural pressure vessels performs the heating-up step, any one of the other pressure vessels performs the temperature lowering step and allows heat recovery to be made by supplying flash vapor discharged from the pressure vessel performing the temperature lowering step to the pressure vessel performing the heating-up step.

By thus performing the discharging step and the charging step in one pressure vessel, it is possible to reduce the total number of process steps to four and the total number of pressure vessels used to four (or a multiple of four) and shorten the processing time. For this reason, this method and system has the advantage of improving the production capacity. With the hydrolytic saccharification method and system having four steps in total according to the present invention, heat exchange between the high-temperature slurry to be discharged from each vessel and the slurry (raw slurry) to be charged into the same pressure vessel is possible in the discharging and charging step.

Similarly, with the hydrolytic saccharification method and system having four process steps in total according to the present invention, heat exchange between high-temperature water be discharged from each vessel and water to be charged into the same pressure vessel is possible in the discharging and charging step.

In cases where equal time is required to complete respective of all the aforementioned four steps, the number of pressure vessels used is preferably a multiple of four. With this feature, the sequential steps can be performed smoothly while performing heat recovery twice.

In cases where equal time is required to complete respective of all the three steps other than the hydrolyzing step and the time required to complete the hydrolyzing step is n times (where n is a natural number) as long as the time required to complete each of the other three steps, the number of pressure vessels used is preferably a multiple of (3+n). In cases where the time required to complete the hydrolyzing step is n times as long as that required to complete any other step, the number of pressure vessels to perform the hydrolyzing step is preferably n times as large as the number of pressure vessels to perform the other steps. With this feature, the sequential steps can be performed smoothly while performing heat recovery twice.

When the hydrolyzing step is performed at a temperature of not lower than 140° C. and not higher than 180° C., the hydrolytic saccharification method including four process steps in total is also capable of hydrolyzing hemicellulose into saccharides (mainly including C5 monosaccharides).

The slurry resulting from the discharging and charging step is subjected to solid-liquid separation; a solid content produced after elution of hydrolyzed hemicellulose to the solvent side is separated out for use as a fresh raw slurry; the raw slurry is charged into the same pressure vessel again in the discharging and charging step; and the hydrolyzing step is performed at a temperature of not lower than 240° C. and not higher than 280° C. By so doing, cellulose can be hydrolyzed into saccharides (mainly including C6 monosaccharides).

Alternatively, by subjecting the water-permeable vessel having been subjected to the discharge step to the charging step again and performing the hydrolyzing step at a temperature of not lower than 240° C. and not higher than 280° C., it is possible to hydrolyze cellulose into saccharides.

When the hydrolyzing step is performed at a temperature of not lower than 240° C. and not higher than 280° C., cellulose can be hydrolyzed into saccharides (mainly including C6 monosaccharides).

Preferably, the discharging and charging step includes addition of ethanol in an amount of not less than 2 mol % and not more than 10 mol % to the raw slurry or to water to be encapsulated into each pressure vessel. The reasons that the aforementioned temperature conditions and the addition of ethanol are preferable are as stated above for the charging step of the hydrolytic saccharification method including five process steps in total.

Ethanol added to the raw slurry is mostly transferred to flash vapor in the temperature lowering step and then collected into the slurry in another pressure vessel performing the heating-up step. The aqueous solution containing saccharides, which is removed out of each pressure vessel by the discharging step, is subjected to ethanol fermentation and thereby converted to bioethanol. If ethanol remains in the initial phase of ethanol fermentation, fermentation by yeast is inhibited by such residual ethanol. The inventions have the feature that ethanol fermentation is difficult to inhibit because the method can reduce the amount of ethanol in the slurry containing cellulose and/or hemicellulose which is obtained after the discharging step while keeping a desired ethanol concentration in the hydrolyzing step.

As disclosed in patent document 4 or 5, when the medium comprising alcohol or the like as a major component is brought into its subcritical condition, the internal pressure of the pressure vessel becomes as high as or higher than 12 MPa at 280° C. for example. With the invention according to, in contrast, the internal pressure of the pressure vessel reaches no more than about 7.5 to about 9.7 MPa at 280° C., which the same temperature. Thus, the method according to this invention is capable of saving the pressurizing energy while allowing the pressure resistance of the pressure vessel to lower, thereby offering an economical merit.

The foregoing and other objects, features and attendant advantages of the present invention will become more apparent from the reading of the following detailed description of the invention in conjunction with the accompanying drawings.

ADVANTAGE OF THE INVENTION

According to the present invention, cellulose and/or hemicellulose contained in a cellulosic biomass can be hydrolyzed into saccharides in a high yield at a low cost with use of plural pressure vessels. Also, the present invention can save the required calorie by about 60% and hence has a very excellent economical merit because waste heat can be easily recovered from a pressure vessel performing another step and utilized for preheating to a suitable temperature for hydrolytic saccharification reaction.

By charging a cellulosic biomass into the water-permeable vessel and encapsulating the water-permeable vessel and water into each pressure vessel, it is possible to prevent piping and the like from being stained as well as to improve the operating efficiency further.

DETAILED DESCRIPTION OF THE PREFERRED EMBODIMENTS

Hereinafter, embodiments of the present invention will be described with appropriate reference to the drawings. It is to be noted that the present invention is not limited to the embodiments described below.

Embodiment 1

Figure 1:
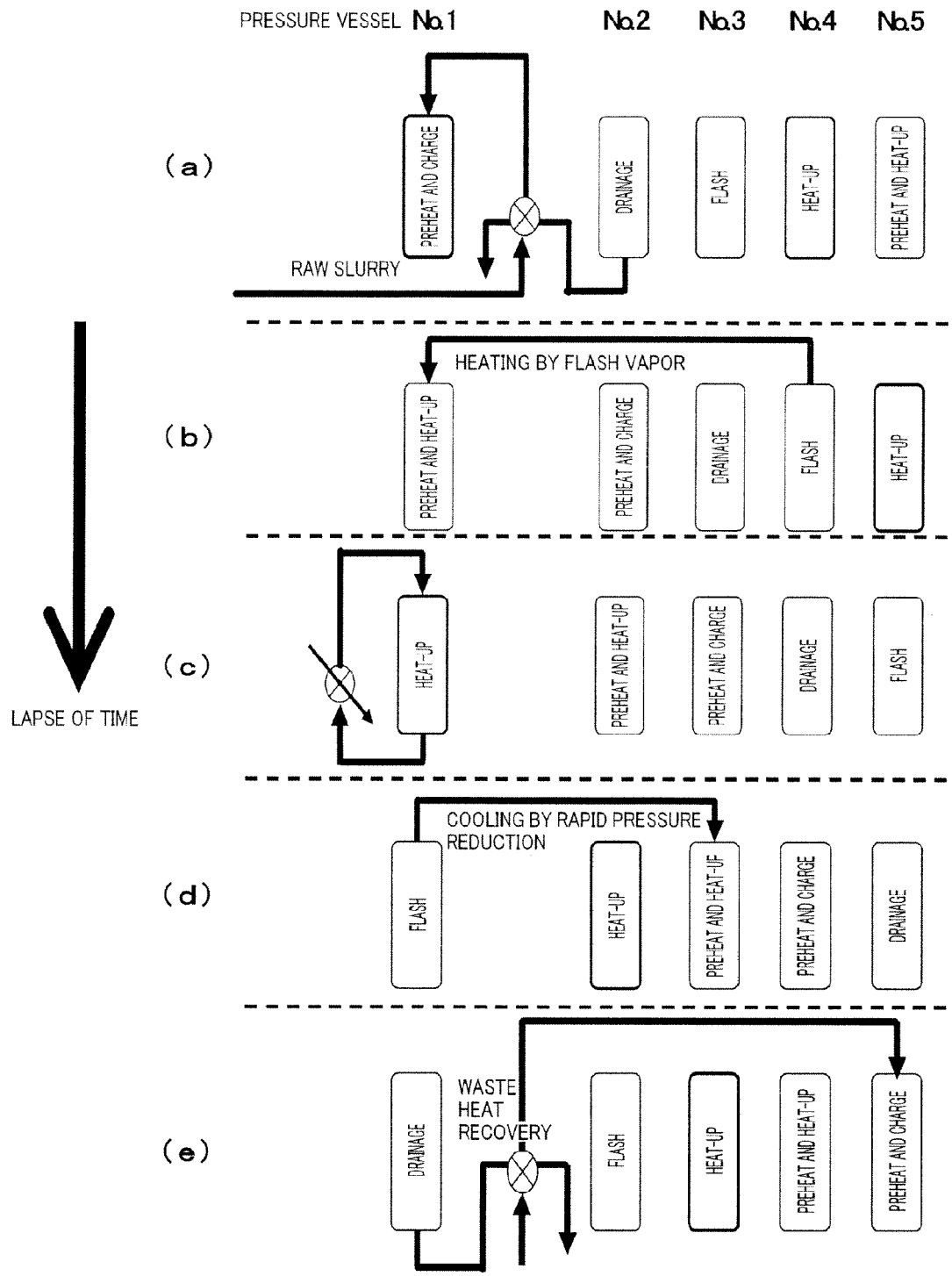
FIG. 1 is a chart illustrating a procedure for operating a hydrolytic saccharification system according to embodiment 1.

Referring to FIG. 1, description will be made of a procedure for operating a hydrolytic saccharification system configured to perform five process steps in total and use five pressure vessels according to embodiment 1.

First, a cellulosic biomass (for example, a vegetation biomass comprising bagasse, sugar beet residue, straws or the like) is ground to sizes of not more than several millimeters and then mixed with water or a dilute ethanol aqueous solution (2 to 10 mol %) to prepare a slurry having a solid matter concentration of about 30%. The slurry thus obtained (raw slurry) is charged into pressure vessel No. 1, as shown in FIG. 1(a) (charging step). Since there is no thermal energy released from any other pressure vessel at the time the hydrolytic saccharification system starts operating, the raw slurry cannot be preheated by heat exchange.

Pressure vessels Nos. 1 to 5 each repeatedly perform the sequence of process steps: charging step→heating-up step→hydrolyzing step→temperature lowering step→discharging step, and four pressure vessels Nos. 2 to 5 each operate with a time lag corresponding to one process step. In the case of FIGS. 1(a) to 1(e), when pressure vessel No. 1 is at the charging step, pressure vessels Nos. 2 to 5 are at the discharging step, temperature lowering step, hydrolyzing step and heating-up step, respectively.

In FIGS. 1(a) to 1(e), the terms "preheat and charge", "preheat and heat-up", "heat-up", "flash" and "drainage" represent the charging step, heating-up step, hydrolyzing step, temperature lowering step and discharging step, respectively.

In cases where the hydrolytic saccharification system is already in operation and the second or later charging step is to be performed by pressure vessel No. 1, heat exchange is allowed to occur between a slurry (containing saccharides) to be discharged (or drained) from pressure vessel No. 2 at the discharge step and the raw slurry to be charged into pressure vessel No. 1, thereby preheating the raw slurry.

Subsequently, pressure vessel No. 1 is closed hermetically (heating-up step). At that time pressure vessel No. 4 is at the temperature lowering step as shown in FIG. 1(b). For this reason, high-temperature gas present in an upper portion of pressure vessel No. 4 is supplied as flash vapor to pressure vessel No. 1 in order to recover heat. (As described above, flash vapor is preferably supplied into the aqueous solution contained in the pressure vessel.) As a result, the temperature of the slurry contained in pressure vessel No. 1 is raised further, whereby the energy required to bring the slurry into its subcritical condition can be saved.

Subsequently, the interior of pressure vessel No. 1 is heated using a heat source, such as high-temperature steam, to bring the slurry into its subcritical condition, as shown in FIG. 1(c) (hydrolyzing step). Preferably, ethanol is previously added to the raw slurry to a concentration of not less than 2 mol % and not more than 10 mol %. The addition of ethanol allows the hydrolysis reaction rate to be lowered, thereby making it easy to control the hydrolysis reaction of cellulose or hemicellulose in the hydrolyzing step.

The "hydrolyzing step", as used in the present invention, is meant to include not only the time during which the slurry is in the subcritical condition but also the time required to heat the slurry having been raised in temperature by the heating-up step until the slurry is brought into the subcritical condition.

If ethanol is added to the raw slurry to a concentration of more than 10 mol %, the hydrolysis time becomes longer than necessary while at the same time the pressure vessel needs to have a higher pressure resistance. In addition, the slurry discharged (or drained) by the discharging step contains a high concentration of residual ethanol. For these reasons, the addition of too much ethanol impairs the practical value of the invention.

Subsequently, pressure vessel No. 1 having passed a proper hydrolysis time is connected to pressure vessel No. 3 at the preheating step in order to supply, as flash vapor, the high-temperature slurry present in a lower portion of pressure vessel No. 1 into pressure vessel No. 3, as shown in FIG. 1(d). By so doing, the interior of pressure vessel No. 1 is rapidly cooled to a temperature below the hydrolytic saccharification temperature, thereby making it possible to stop degradation reaction of saccharides into organic acids or the like. At the same time, the temperature of the slurry in pressure vessel No. 3 is raised.

In order for hemicellulose contained in the biomass to be hydrolytically saccharificated in the hydrolyzing step, the temperature of the slurry is adjusted to within the temperature range of from 140° C. to 180° C. which allows only hemicellulose to be hydrolytically saccharificated, without being raised to within the temperature range (240° C. to 280° C.) which allows cellulose to be hydrolytically saccharificated. On the other hand, in order for cellulose contained in the biomass to be hydrolytically saccharificated, the temperature of the slurry is raised to within the temperature range (240° C. to 280° C.) which allows cellulose to be hydrolytically saccharificated.

Subsequently, pressure vessel No. 1 of which the temperature has lowered and of which the pressure has lowered to a normal pressure or a pressure close to the normal pressure is opened and the slurry containing saccharides is discharged (or drained) therefrom, as shown in FIG. 1(e) (discharging step). In the case of the slurry having been subjected to a temperature of from 240° C. to 280° C. in the hydrolyzing step, the temperature of the slurry in the discharging step is about 110° C. to about 150° C. For this reason, heat exchange is allowed to occur between the slurry in pressure vessel No. 1 at the discharging step and the slurry to be charged into pressure vessel No. 5. By so doing, it is possible to preheat the slurry to be charged into pressure vessel No. 5 as well as to cool the slurry to be removed out of pressure vessel No. 1.

While description has been made mainly of the operating procedure for pressure vessel No. 1 with reference to FIGS. 1(a) to 1(e), pressure vessels Nos. 2 to 5 are each operated according to the same procedure. With respect to the pressure vessels other than pressure vessel No. 1, the waste heat recovery (i.e., heat exchange) operations using flash vapor and high-temperature slurry are partly omitted from FIGS. 1(a) to (e). However, it is needless to say that waste heat recovery (i.e., heat exchange) is performed for each of these pressure vessels in the same manner as for pressure vessel No. 1.

Saccharides and residual solid content coexist in the slurry discharged (or drained) by the discharging step and cooled by heat exchange. Where the hydrolyzing step temperature is within the range of from 140° C. to 180° C., the residual solid content comprises cellulose and lignin as major components. Where the hydrolyzing step temperature is within the range of from 240° C. to 280° C., the residual solid content comprises lignin as a major component.

After the residual solid content of the slurry has been removed away by solid-liquid separation, the resulting liquid is subjected to ethanol fermentation utilizing the fermentation action and the like of yeast, thus giving bioethanol. Since such an ethanol fermentation technique is well-known, description thereof is omitted herein. Saccharides obtained by the present invention can be converted to bioethanol by a known fermentation process other than yeast fermentation.

Figure 2:
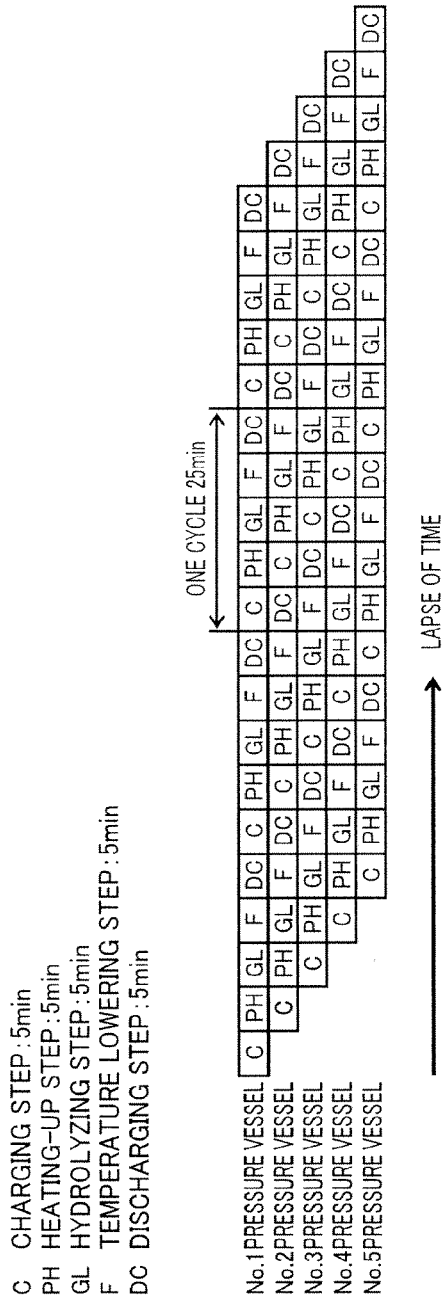
FIG. 2 is a time schedule chart for operating the hydrolytic saccharification system of embodiment 1 as a sequencing batch system.

Referring to FIG. 2, description will be made of a time schedule for operating the hydrolytic saccharification system using the five pressure vessels shown in FIGS. 1(a) to 1(b) as a sequencing batch system. In FIG. 2, the time required to complete each process step is five minutes.

Initially, pressure vessel No. 1 performs the charging step and, subsequently, pressure vessels Nos. 2 to 5 perform the charging step sequentially with a time lag of five minutes from one pressure vessel to the next one. Each pressure vessel repeats the five sequential steps: [C]→[PH]→[GL]→[F]→[DC] and, accordingly, one cycle of the hydrolytic saccharification process for a cellulosic biomass is 5 min×5 steps=25 minutes. Pressure vessels Nos. 1 to 5 perform this cycle sequentially with a time lag of five minutes from one pressure vessel to the next one.

Flashing vapor contained in pressure vessel No. 1 at the temperature lowering step is supplied to pressure vessel No. 2 at the heating-up step, thus making heat recovery. Likewise, flashing vapor contained in each of pressure vessels Nos. 2 to 5 at the temperature lowering step is supplied to a respective one of pressure vessels Nos. 3, 4, 5 and 1, thus making heat recovery.

The slurry to be discharged (or drained) from pressure vessel No. 1 at the discharging step exchanges heat with the slurry to be charged into pressure vessel No. 5 at the charging step. Likewise, the high-temperature slurry contained in each of pressure vessels Nos. 2 to 5 at the discharge step exchanges heat with the slurry to be charged into a respective one of pressure vessels Nos. 1 to 4 at the charging step.

Such a sequencing batch system makes it possible to hydrolytically saccharificate a biomass in a short time with the required energy saved.

Embodiment 2

Figure 3:
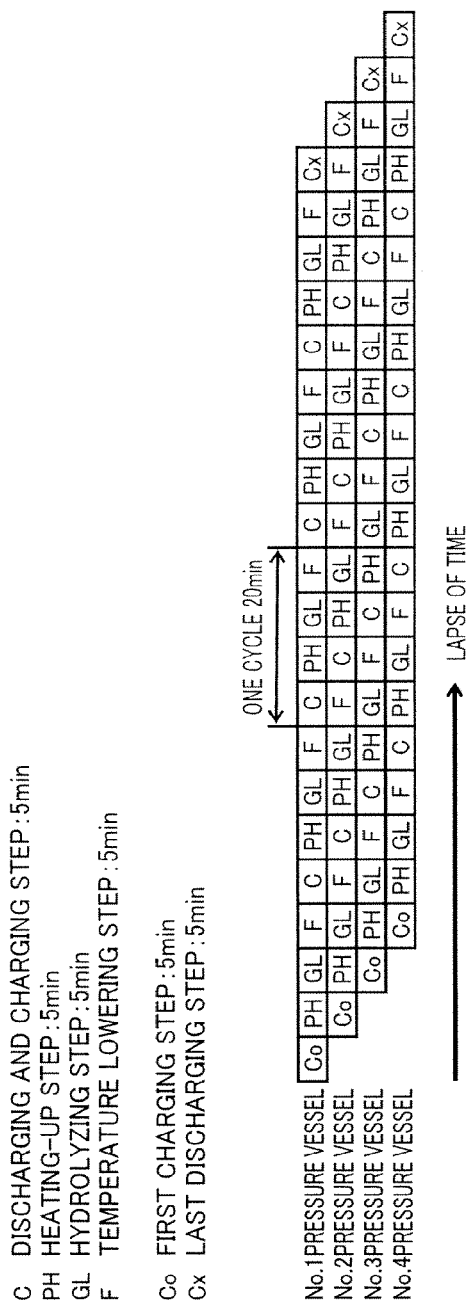
FIG. 3 is a time schedule chart for operating a hydrolytic saccharification system of embodiment 2 as a sequencing batch system.

Referring to FIG. 3, description will be made of a time schedule for operating a hydrolytic saccharification system as a sequencing batch system, the hydrolytic saccharification system being configured to perform four steps in total and use four pressure vessels each configured to perform the discharging step and the charging step in parallel as a discharging and charging step in a steady operation. In FIG. 3, the time required to complete each step is five minutes.

Initially, pressure vessel No. 1 performs the first charging step Co and, subsequently, pressure vessels Nos. 2 to 4 perform the first charging step Co sequentially with a time lag of five minutes from one pressure vessel to the next one. When the system starts operating, the system performs the same charging step as does the hydrolytic saccharification system shown in FIG. 1. For this reason, the discharging and charging step performed first is referred to as "first charging step Co" in FIG. 3. In steady operation, each pressure vessel repeats the four sequential steps: [C]→[PH]→[GL]→[F] and, accordingly, one cycle of the hydrolytic saccharification process for a cellulosic biomass is 5 min×4 steps=25 minutes. Pressure vessels Nos. 1 to 4 perform this cycle sequentially with a time lag of five minutes from one pressure vessel to the next one.

Flashing vapor contained in pressure vessel No. 1 at the temperature lowering step is supplied to pressure vessel No. 2 at the heating-up step, thus making heat recovery. Likewise, flashing vapor contained in each of pressure vessels Nos. 2 to 4 at the temperature lowering step is supplied to a respective one of pressure vessels Nos. 3 to 5 at the heating-up step, thus making heat recovery.

The slurry is removed out of pressure vessel No. 1 at the discharging and charging step after the temperature lowering step and then a raw slurry is charged into the same pressure vessel. That is, pressure vessel No. 1 having completed the temperature lowering step performs the discharging step and the charging step in parallel. When the temperature of the slurry to be discharged is sufficiently high, heat exchange with the raw slurry to be charged may be made.

In terminating the operation, pressure vessel No. 1 having completed the last temperature lowering step performs the last discharging step Cx and, subsequently, pressure vessels Nos. 2 to 4 perform the last discharging step Cx sequentially with a time lag of five minutes from one pressure vessel to the next one. In terminating the operation of the system, the system performs the same discharging step as does the hydrolytic saccharification system shown in FIG. 1. For this reason, the discharging and charging step performed last is referred to as "the last discharging step Cx" in FIG. 3.

This sequencing batch system is capable of achieving continuous hydrolytic saccharification in a shorter time with fewer pressure vessels than the hydrolytic saccharification system shown in FIGS. 1 and 2.

Effect of the Addition of Ethanol in the Hydrolyzing Step

Figure 4:
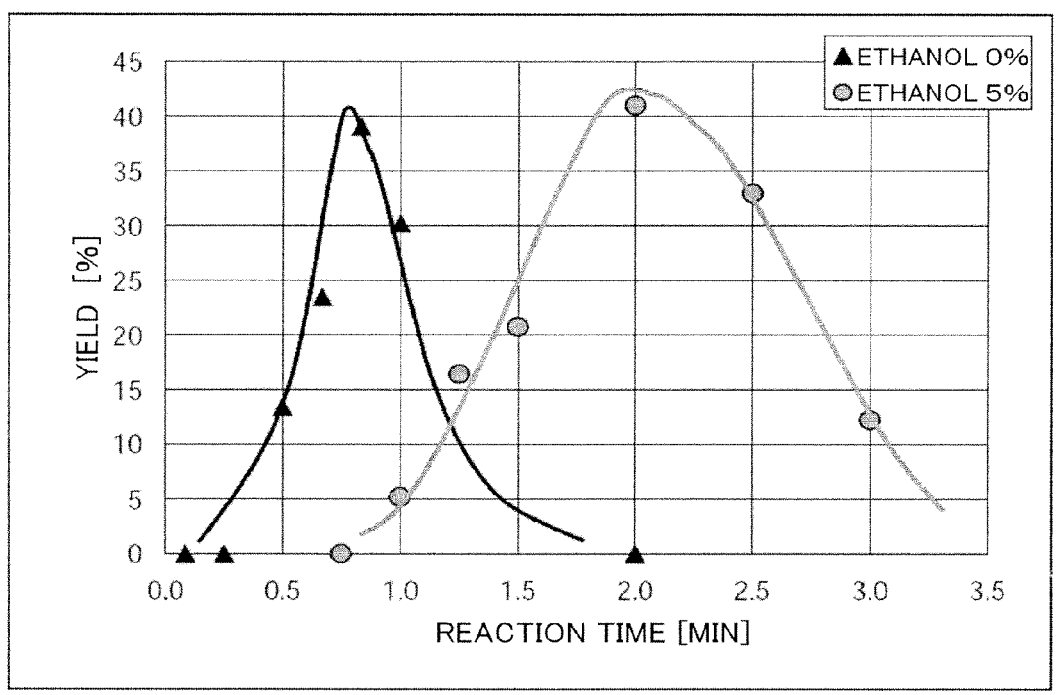
FIG. 4 is a graph plotting the relationship between the reaction time of hydrolytic saccharification of a biomass and the yield of saccharides (%)

Effect of the addition of ethanol on hydrolytic saccharification of reagent cellulose under the subcritical condition was studied with the reagent cellulose used as a biomass. FIG. 4 shows the result of an experiment in which pure water and 5 wt % (2 mol %) ethanol aqueous solution, which were at the same temperature of 280° C., were each passed through the above-noted cellulose.

FIG. 4 shows the relationship between the reaction time and the yield of saccharides (%). The addition of ethanol was found to have substantially no effect on the maximum yield of saccharides. With respect to the saccharide production rate and the hydrolysis rate, however, they were apparently lowered by the addition of ethanol. For example, the time required to reach the maximum yield was increased about three times (0.7 min→2.0 min) by the addition of ethanol.

It is difficult for an industrial-scale system to control the reaction time under the subcritical condition to the second. For this reason, the addition of ethanol to a raw slurry was confirmed effective in raising the yield of saccharides.

Embodiment 3

Figure 5:
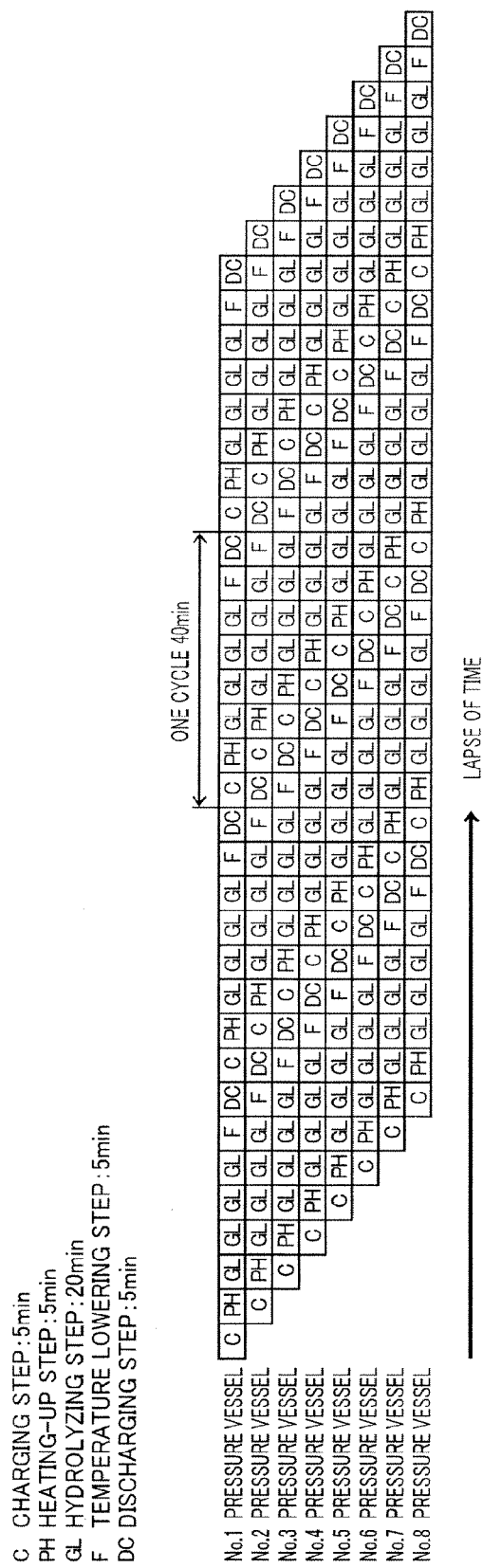
FIG. 5 is a time schedule chart for operating a hydrolytic saccharification system of embodiment 3 as a sequencing batch system.

Referring to FIG. 5, description will be made of a time schedule for operating a hydrolytic saccharification system as a sequencing batch system, the hydrolytic saccharification system being configured to perform five steps in total and use eight pressure vessels. This system is adapted to cases where a cellulosic biomass is difficult to hydrolytically saccharificate under the subcritical condition and, hence, the hydrolyzing step cannot but be performed for a longer time than the other four steps. In FIG. 5, the time required to complete the hydrolyzing step is 20 minutes and that required to complete any other step is five minutes.

Initially, pressure vessel No. 1 performs the charging step and, subsequently, pressure vessels Nos. 2 to 8 perform the charging step sequentially with a time lag of five minutes from one pressure vessel to the next one. Each pressure vessel repeats the five sequential steps: [C]→[PH]→[GL]→[F]→[DC]. Here, the time required to complete the step of hydrolyzing a cellulosic biomass into saccharides is 20 minutes and, accordingly, one cycle of the hydrolytic saccharification process is (5 min×4 steps)+(20 min×1 step)=40 minutes. Pressure vessels Nos. 1 to 8 perform this cycle sequentially with a time lag of five minutes from one pressure vessel to the next one.

With the sequencing batch system shown in FIG. 5, the time required to complete the hydrolyzing step is four times as long as that required to complete any other process step. Therefore, if five pressure vessels, the number of which corresponds to the five process steps, are used, the thermal energy of flash vapor and that of high-temperature slurry cannot be recovered unless each of the process steps other than the hydrolyzing step takes 20 minutes as does the hydrolyzing step. For this reason, the processing time would be very long. In view of such an inconvenience, the hydrolytic saccharification system according to the present embodiment uses eight pressure vessels to realize effective heat recovery while taking five minutes for any other process step than the hydrolyzing step as does the foregoing system and 20 minutes for the hydrolyzing step.

When pressure vessel No. 1 is at the temperature lowering step, flashing vapor contained in pressure vessel No. 1 is supplied to pressure vessel No. 6 at the heating-up step. Likewise, flashing vapor contained in each of pressure vessels Nos. 2 to 8 at the temperature lowering step is supplied to a respective one of pressure vessels Nos. 7, 8, 1, 2, 3, 4 and 5, thus making heat recovery.

The high-temperature slurry to be discharged (or drained) from pressure vessel No. 1 at the discharging step exchanges heat with the slurry to be charged into pressure vessel No. 8 at the charging step. Likewise, the high-temperature slurry to be discharged from each of pressure vessels Nos. 2 to 8 at the discharge step exchanges heat with the slurry to be charged into a respective one of pressure vessels Nos. 1 to 7.

In cases where equal time is required to complete respective of the four steps other than the hydrolyzing step and the time required to complete the hydrolyzing step is n times (where n is a natural number; n is four in this example) as long as the time required to complete each of the other four steps, the number of pressure vessels used is preferably a multiple of (4+n). The system thus arranged a sequencing batch system is capable of achieving continuous hydrolytic saccharification of a cellulosic biomass in a short time with the required energy saved, like embodiment 1.

While embodiment 3 uses eight pressure vessels, the hydrolytic saccharification system, when comprising two sequencing bath systems, may use 16 pressure vessels in total. The hydrolytic saccharification system configured to perform four process steps in total may be operated in a similar manner as above.

Embodiment 4

With respect to the foregoing embodiments 1 to 3, description has been directed to the cases where a cellulosic biomass is ground and then mixed with water to prepare a slurry, which is then charged into a pressure vessel in the charging step or the discharging and charging step. In the charging step or the discharging and charging step according to the present invention, however, a cellulosic biomass need not necessarily be slurried. Hydrolysis saccharification of a cellulosic biomass can be achieved also by such a charging step or discharging and charging step which includes: charging a cellulosic biomass, such as bagasse, into a water-permeable vessel having perforations, apertures or the like for allowing water to move from the exterior to the interior of the water-permeable vessel and vice versa; and encapsulating the water-permeable vessel and water into each pressure vessel (compressive and dense encapsulation).

Though there is no limitation on the material of the water-permeable vessel as long as the material can withstand elevated temperatures in the pressure vessel, the material is preferably stainless steel and a like material having a high endurance. Also, there is no limitation on the shape of the water-permeable vessel; for example, a rectangular-parallelepiped shape, a cylindrical shape or the like may be appropriately selected for the water-permeable vessel. However, the same shape as the internal shape (cylindrical shape) of each pressure vessel is preferable in view of its high volumetric efficiency. Any means for ensuring the water-permeability may be employed without any particular limitation as long as the water-permeable vessel allows water to move from the exterior to the interior of the water-permeable vessel and vice versa; for example, the water-permeable vessel may be partially or entirely reticulated; the water-permeable vessel may be formed with slits or circular perforations; or the water-permeable vessel may have open top.

Figure 6:
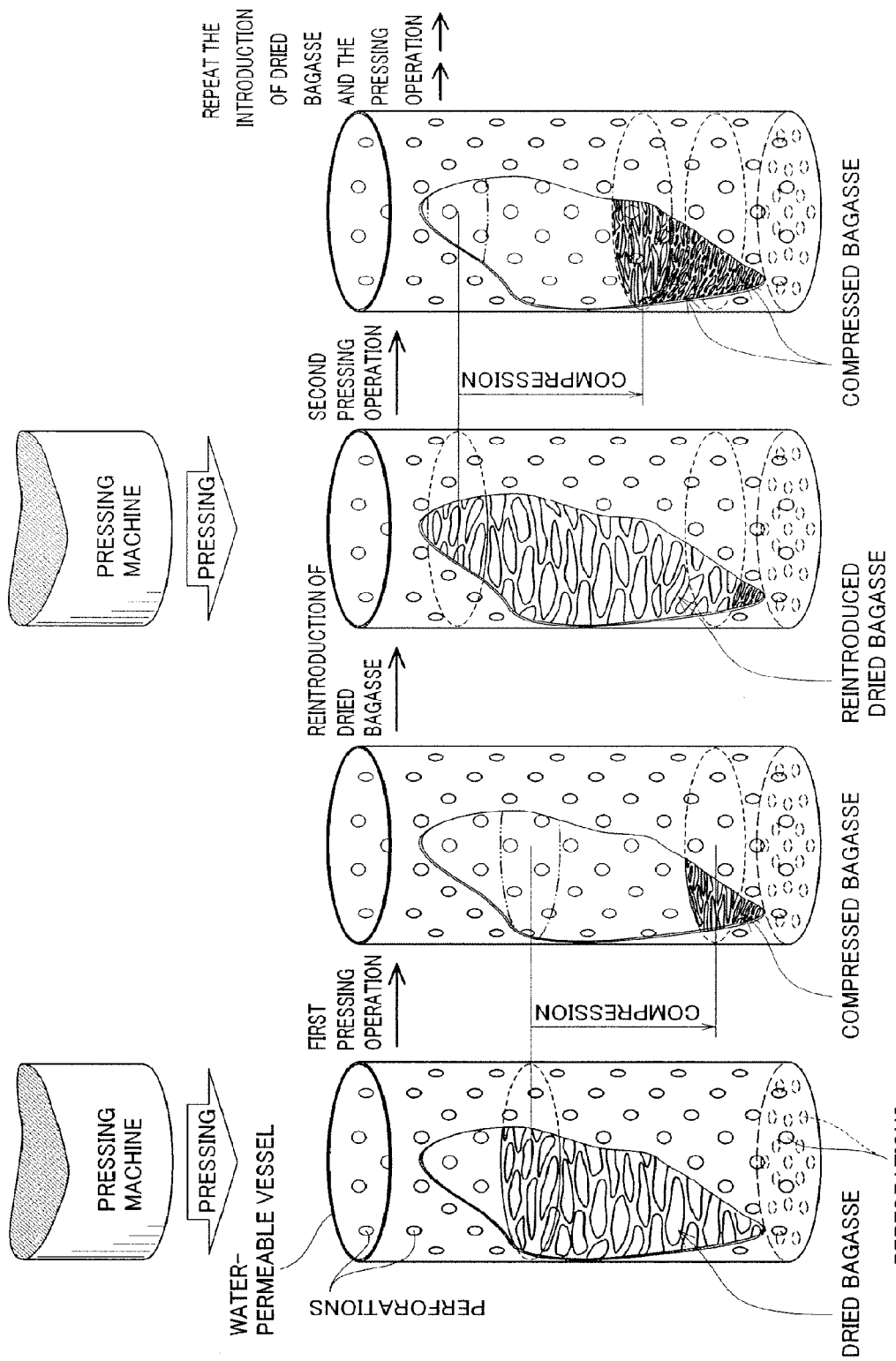
FIG. 6 is a view illustrating an example in which dried bagasse is compressively and densely charged into a water-permeable vessel according to embodiment 4.

FIG. 6 illustrates an example in which dried bagasse as a cellulosic biomass is charged into the water-permeable vessel. In this figure, the water-permeable vessel to be charged with bagasse has a cylindrical shape (with open top) having a bottom surface and a peripheral surface, which are formed with multiple perforations. In this case there is no need to grind the dried bagasse. The dried bagasse may be used with its length left as it is or cut to an appropriate length.

After charging, it is preferable to compress the dried bagasse within the water-permeable vessel from above by means of a pressing machine or the like. The dried baggase in a previously compressed condition may be charged into the water-permeable vessel. The dried bagasse, which has a bulk specific gravity of about 5 to about 10 kg/m3 before compression, can be compressed to a bulk specific gravity of not less than 50 kg/m3. The dried bagasse in this compressed condition is encapsulated into each pressure vessel and then water is poured into the pressure vessel to capacity. By so doing, the interior of the pressure vessel has a solid matter concentration of about several %, which is the same level of solid matter concentration as the slurry. Therefore, the pressure vessel has substantially the same volumetric efficiency as with the dried bagasse in the form of slurry.

In compressing dried bagasse within the water-permeable vessel, it is preferable that the water-permeable vessel is compressively and densely charged with dried bagasse as much as possible by repeating the introduction of dried bagasse into the water-permeable vessel and the pressing operation. The pressing operation may be performed only once as long as a sufficient amount of dried bagasse can be compressively and densely charged into the water-permeable vessel.

The bulk specific gravity of a cellulosic biomass, such as dried baggase, is preferably adjusted to a value of not less than 50 kg/m3 and not more than 300 kg/m3, more preferably not less than 100 kg/m3 and not more than 200 kg/m3, before encapsulation into the pressure vessel. If the bulk specific gravity of the cellulosic biomass is too low, the solid matter concentration becomes lower than that of the cellulosic biomass in the form of slurry, which results in a lowered volumetric efficiency. On the other hand, if the bulk specific gravity of the cellulosic biomass is too high, it is difficult for water to penetrate into the cellulosic biomass and, hence, the hydrolysis reaction of the cellulosic biomass occurs with difficulty.

In slurrying a cellulosic biomass such as dried bagasse, the energy required to pulverize the cellulosic biomass is about 0.5 to 2 kW per 1 kg of the raw material. Such a pulverizing operation is eliminated in the present embodiment. Even if grinding is necessary, pulverization is not required. The amount of work required to pretreat the cellulosic biomass is reduced to $\frac{1}{10}$ to $\frac{1}{2}$.

In charging the cellulosic biomass in the form of slurry into a pressure vessel, it is required that the solid matter concentration be lowered or the cellulosic biomass be pulverized in order to prevent the piping from being clogged. The cellulosic biomass has a relatively high water content. For this reason, even when the solid matter concentration of the slurry is about 10% with the water content of the cellulosic biomass taken into consideration, the flowability of the slurry is low. However, by encapsulating the water-permeable vessel charged with the cellulosic biomass into the pressure vessel together with water, the solid matter concentration within the pressure vessel can be made substantially equal to that of the slurry, as described above.

With the cellulosic biomass in the form of slurry, solid matter is sometimes deposited on the inner wall of the piping as well as on the inner wall of the pressure vessel and remains thereon as residual solid matter. Such residual solid matter not only causes the volumetric efficiency of each of the piping and the pressure vessel but also mixes, as reacted fine powder, into unreacted slurry. Therefore, such residual solid matter causes the frequency of cleaning to increase. However, such a problem will not arise by virtue of the step of encapsulating the water-permeable vessel charged with the cellulosic biomass into the pressure vessel together with water, followed by heating because only water passes through the piping with the cellulosic biomass left within the water-permeable vessel.

Further, in cases where the cellulosic biomass is heated at a temperature of not lower than 140° C. and not higher than 180° C. to hydrolyze hemicellulose into saccharides and then the residual solid matter is heated at a temperature of not lower than 240° C. and not higher than 280° C. to hydrolyze cellulose into saccharides, it is required that the solid content obtained after the hydrolysis of hemicellulose be separated out by solid-liquid separation and then mixed with water again to form a slurry when the charging step or the discharging and charging step includes charging the cellulosic biomass in the form of slurry into the pressure vessel. However, with the process of encapsulating the water-permeable vessel charged with the cellulosic biomass into the pressure vessel together with water and then heating the pressure vessel, there are advantages that it is sufficient to discharge water containing saccharides and that the water-permeable vessel serves also as the means for solid-liquid separation. By collecting water containing saccharides that remains together with the biomass residue in the water-permeable vessel by washing the biomass residue, it is possible to collect saccharides more efficiently.

In cases where the water-permeable vessel charged with the cellulosic biomass is encapsulated into the pressure vessel together with water in the charging step or the discharging and charging step, the discharging step or the discharging and charging step includes: discharging high-temperature water containing saccharides; removing the water-permeable vessel out of the pressure vessel; and removing a solid residue (which is a residual solid matter left after hydrolysis of cellulose and/or hemicellulose contained in the cellulosic biomass and comprising lignin and an ash content as major components), followed by disposal.

Since this residue can be utilized as a fuel for heating the interior of the pressure vessel, the present embodiment, according to which the solid matter concentration within the pressure vessel can be raised and, hence, the amount of residue removed out of the pressure vessel can be increased, is capable of suppressing the amount of fuel to be used, such as petrol.

In the temperature lowering step, high-temperature water contained in the pressure vessel is flash-evaporated to exchange heat with water to be charged into the pressure vessel performing the charging step. Other features are similar to the corresponding features of the method and system in which the cellulosic biomass in the form of slurry is charged by the charging step or the discharging and charging step.

For example, in the case of the charging step in which the cellulosic biomass is charged into the water-permeable vessel and then encapsulated into the pressure vessel together with water, the "water and water-permeable vessel charged with the cellulosic biomass" is equivalent to the "raw slurry" appearing in FIG. 1 illustrating the procedure for operating the hydrolytic saccharification system of embodiment 1.

It will be apparent from the foregoing description that many improvements and other embodiments of the present invention may occur to those skilled in the art. Therefore, the foregoing description should be construed as an illustration only and is provided for the purpose of teaching the best mode for carrying out the present invention to those skilled in the art. The details of the structure and/or the function of the present invention can be modified substantially without departing from the spirit of the present invention.

Industrial Applicability

The present invention is useful as a method and system for hydrolyzing a cellulosic biomass into saccharides, to be applied in industrial fields such as the bioindustry and energy industry.

What is claimed is:

1. A batch wise method of hydrolytic saccharification of a cellulosic biomass with use of plural pressure vessels, the method comprising a charging step, a heating up step, a hydrolyzing step, a temperature lowering step, and a discharging step, which are performed sequentially by each of said pressure vessels; wherein:

said charging step is a step of charging said cellulosic biomass into a water permeable vessel and then encapsulating said water permeable vessel and water into each of said pressure vessels;

said heating up step is a step of hermetically closing the pressure vessel and heating up said cellulosic biomass and water;

said hydrolyzing step is a step of hydrolyzing cellulose and/or hemicellulose contained in said cellulosic biomass into saccharides by an oxidative power of high temperature and high pressure water;

said temperature lowering step is a step of flash evaporating high temperature and high pressure water contained in the pressure vessel to lower the temperature thereof;

said discharging step is a step of removing said water and said water permeable vessel out of said pressure vessel;

equal time is required to complete respective of all the four steps other than said hydrolyzing step; the time required to complete said hydrolyzing step is n times (where n is a natural number) as long as the time required to complete each of the other four steps; and the number of the pressure vessels used is a multiple of (4+n), and while any one of said plural pressure vessels performs said charging step, any one of the other pressure vessels performs said discharging step so as to allow heat exchange to occur between water to be charged into the pressure vessel performing said charging step and high temperature water to be discharged from the pressure vessel performing said discharging step; and while any one of said plural pressure vessels performs said heating up step, any one of the other pressure vessels performs said temperature lowering step and allows heat recovery to be made by supplying flash vapor discharged from the pressure vessel performing said temperature lowering step to the pressure vessel performing said heating up step.

2. The batch wise method according to claim 1, wherein said hydrolyzing step is performed at a temperature of not lower than 140° C. and not higher than 180° C. to hydrolyze hemicellulose into saccharides.

3. The batch wise method according to claim 2, wherein said water permeable vessel having been subjected to said discharging step is subjected to said charging step again and said hydrolyzing step is performed at a temperature of not lower than 240° C. and not higher than 280° C. to hydrolyze cellulose into saccharides.

4. The batch wise method according to claim 1, wherein said hydrolyzing step is performed at a temperature of not lower than 240° C. and not higher than 280° C. to hydrolyze cellulose into saccharides.

5. The batch wise method according to claim 1, wherein said charging step includes addition of ethanol in an amount of not less than 2 mol % and not more than 10 mol % to said water.

* * * * *